(12) United States Patent
Lazzari et al.

(10) Patent No.: US 9,249,169 B2
(45) Date of Patent: Feb. 2, 2016

(54) PROCESS FOR THE PREPARATION OF PHOSPHONIUM SULFONATES

(71) Applicant: MITENI S.p.A., Trissino (IT)

(72) Inventors: Dario Lazzari, Trissino (IT); Simonetta Mondini, Trissino (IT); Marisa Pretto, Trissino (IT); Francisco Casado Moreno, Trissino (IT); Andrea Faccin, Trissino (IT); Camillo Zarantonello, Trissino (IT)

(73) Assignee: MITENI S.P.A., Milan (IT)

( * ) Notice: Subject to any disclaimer, the term of this patent is extended or adjusted under 35 U.S.C. 154(b) by 0 days.

(21) Appl. No.: 14/409,230

(22) PCT Filed: Jul. 10, 2013

(86) PCT No.: PCT/IB2013/001496
§ 371 (c)(1),
(2) Date: Dec. 18, 2014

(87) PCT Pub. No.: WO2014/016657
PCT Pub. Date: Jan. 30, 2014

(65) Prior Publication Data
US 2015/0175638 A1    Jun. 25, 2015

(30) Foreign Application Priority Data
Jul. 24, 2012 (IT) ............... MI2012A1283

(51) Int. Cl.
*C07F 9/54* (2006.01)
*C07C 303/32* (2006.01)

(52) U.S. Cl.
CPC .............. *C07F 9/5449* (2013.01); *C07C 303/32* (2013.01); *C07F 9/5407* (2013.01)

(58) Field of Classification Search
CPC ........................... C07F 9/5449; C07C 303/32
USPC .......................................................... 558/54
See application file for complete search history.

(56) References Cited

U.S. PATENT DOCUMENTS 7,429,628 B2 *   9/2008   Hoeks ................... C07C 303/32
                                                          524/115

FOREIGN PATENT DOCUMENTS

EP          0 182 574         5/1986
WO       WO 2008/108983       9/2008

OTHER PUBLICATIONS

International Preliminary Report on Patentability issued in International Application No. PCT/IB2013/001496 dated Jan. 27, 2015.
International Search Report for PCT/IB2013/001496 mailed Oct. 28, 2013.
Search Report for IT MI20121283, dated Apr. 16, 2013, 2 pages.
Written Opinion of the International Searching Authority for PCT/IB2013/0014962, mailed Oct. 28, 2013.

* cited by examiner

*Primary Examiner* — Kristin Vajda
(74) *Attorney, Agent, or Firm* — Nixon & Vanderhye P.C.

(57) ABSTRACT

The invention relates to a process for the preparation of phosphonium sulfonates, particularly tetraalkylphosphonium fluoroalkylsulfonates, in the presence of amine-type bases.

14 Claims, No Drawings

PROCESS FOR THE PREPARATION OF PHOSPHONIUM SULFONATES

This application is the U.S. national phase of International Application No. PCT/IB2013/001496 filed 10 Jul. 2013 which designated the U.S. and claims priority to Italian Patent Application No. MI2012A001283 filed 24 Jul. 2012, the entire contents of each of which are hereby incorporated by reference.

SUMMARY OF THE INVENTION

The present invention relates to a process for the preparation of phosphonium sulfonates, particularly tetraalkylphosphonium fluoroalkylsulfonates, in the presence of amine-type bases.

TECHNICAL BACKGROUND

Tetraalkylphosphonium fluoroalkylsulfonates are known to be prepared by reactions between sulfonyl derivatives and tetraalkylphosphonium halide derivatives in the presence of bases. These compounds are useful as antistatic agents in polymeric compositions, particularly in plastics such as PET (polyethylene terephthalate), PA (polyamide), PC (polycarbonate), polyketone and mixtures of butadiene-acrylonitrile-styrene. For their use as antistatic additives, these compounds are added to polymers either alone or in combination with other additives such as UV absorbers, flame retardants, light stabilizers, antioxidants, etc.

EP1462438 describes the preparation of tetrabutylphosphonium nonafluorobutane-1-sulfonate by combining an aqueous solution of tetrabutylphosphonium halide with an aqueous solution of $(C_4F_9)$-sulfonyl-O- M+, where M is a metal, to give a biphasic mixture which is separated and from which the bottom layer is recovered, preferably by solidification.

EP1737814 describes a process for the preparation of tetrabutylphosphonium nonafluorobutane-1-sulfonate which includes combining $(C_4F_9)$-sulfonyl-O- M+, where M is lithium or sodium, with tetrabutylphosphonium-halide in an aqueous solution.

EP182574 describes a process for the preparation of tetrabutylphosphonium nonafluorobutane-1-sulfonate which includes combining, in an aqueous solution, $(C_4F_9)$-sulfonyl-F with either tetrabutylphosphonium-OH or tetrabutylphosphonium-halide and a base selected from sodium hydroxide and lithium hydroxide.

WO2008108983 describes the reaction between potassium 1,1,2,3,3,3-esafluoropropanesulfonate and tetra-n-butylphosphonium bromide.

The above-mentioned procedures all involve the use of metals from which the desired compounds are difficult to be separated, thereby being very frequently contaminated therewith. The presence of metal traces in the tetraalkylphosphonium fluoroalkylsulfonate compounds leads to serious drawbacks. In fact, for their use as antistatic agents, the above-mentioned compounds should be highly purified because the presence of even a minimum of metal impurities leads to serious consequences in the preparation of plastic materials to which such compounds are added.

OBJECTS OF THE INVENTION

A first object of the invention is to provide a new process for the preparation of phosphonium fluoroalkylsulfonates which is industrially feasible.

Another object of the invention is to provide a process for the preparation of phosphonium fluoroalkylsulfonates which provides such compounds in a pure form.

A further object of the invention is to provide a process for the preparation of phosphonium fluoroalkylsulfonates which provides such compounds in a form free from contamination with metals.

DESCRIPTION OF THE INVENTION

Thus, according to one of its aspects, the invention relates to a new process for the preparation of phosphonium fluoroalkylsulfonates of formula (I)

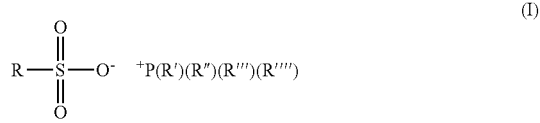

(I)

wherein

R is a straight or branched, saturated or unsaturated, fluoroalkyl group having 1 to 10 carbon atoms, with said fluoroalkyl being optionally interrupted by —O—, —S— or —NR$_1$—, wherein R$_1$ is a hydrogen or a perfluoroalkyl group having 1 to 8 carbon atoms, and R', R", R'" and R"" are the same or different, and each independently represent a hydrogen atom or a straight or branched, saturated or unsaturated, alkyl group having 1 to 10 carbon atoms, with said alkyl being optionally interrupted by —O—, —S— or —NR$_2$— wherein R$_2$ is a hydrogen or an alkyl group having 1 to 10 carbon atoms, comprising reacting a compound of formula (II)

(II)

wherein R is defined as above, with a compound of formula (III)

(III)

wherein R', R", R'" and R"" are defined as above, and X$^-$ represents a halide or a hydroxide ion, in the presence of an amine-type base.

According to the present invention, R is preferably a straight perfluoroalkyl group in which the alkyl is advantageously a straight perfluoroalkyl having 2 to 8 carbon atoms, for example 3 to 6 carbon atoms, even more preferably 4 carbon atoms.

The expression "perfluoroalkyl group" denotes an alkyl group in which all the hydrogen atoms of the alkyl group are replaced by fluorine atoms.

Preferably, according to the present invention, R', R", R'" and R"" are each independently a straight alkyl, advantageously a straight alkyl having 2 to 8 carbon atoms, for example 3 to 6 carbon atoms, even more preferably 4 carbon atoms.

According to another preferred aspect, R', R", R'" and R"" are the same.

According to the present invention, a preferred compound of formula (I) is tetrabutylphosphonium nonafluorobutane-1-sulfonate of formula (Ia)

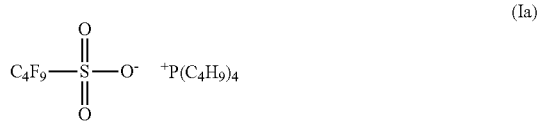

(Ia)

According to a preferred embodiment, the present invention relates to a process for the preparation of a compound of formula (Ia), which comprises reacting perfluorobutylsulfonyl fluoride with tetrabutylphosphonium-bromide in an aqueous medium in the presence of an amine-type base selected from trimethylamine, triethylamine and tributylamine, advantageously at a temperature in the range from 50 to 80° C.

According to the present invention, $X^-$ represents a hydroxide ion ($OH^-$) or a halide selected from $Br^-$, $Cl^-$, $I^-$ and $F^-$, advantageously X is $Br^-$.

According to the present invention, the expression "amine-type base" denotes any basic amine whether it is aliphatic, cycloaliphatic or aromatic in nature. The amine-type base of the present invention includes alkyl-, dialkyl- and trialkyl-amines in which the alkyl may be straight or branched and optionally substituted, such as for example ethanolamine; cycloaliphatic amines such as morpholine, piperazine, piperidine, quinuclidine; aromatic or heteroaromatic amines such as pyridine, aniline.

A particularly preferred amine-type base is selected from trimethylamine, triethylamine and tributylamine, with trimethylamine being particularly preferred.

Optionally, ammonia or ammonium- or alkylammonium-hydroxides may also be used as amine-type bases according to the present invention.

An example of preferred bases is ammonium hydroxide and tetraalkylammonium hydroxides such as tetramethylammonium hydroxide, tetraethylammonium hydroxide, etc.

The presence of the amine-type base is essential for the success of the reaction of the invention. In fact, in absence of a base, the reaction between the two reagents (II) and (III) would not occur. In fact, it is the amine which reacts with water to produce hydroxyl ions which, in turn, transform the sulfonyl fluoride of formula (II) into ammonium sulfonate which is effectively the species reacting with the compound of formula (III) to provide the reaction product which precipitates as a salt thereby separating from the aqueous solution. Furthermore, the choice of the amine base rather than a metal-containing base provides the advantage that no metal traces are left in the final mixture, which is an indispensable factor for obtaining an effective antistatic effect of the compounds of formula (I).

The reaction between the compounds of formula (II) and (III) is preferably carried out in an aqueous medium.

The reaction temperature may vary from room temperature to the reflux temperature of the reaction mixture, advantageously from 30° C. to 80° C. According to a preferred aspect, the reaction of the invention is carried out initially at a temperature of about 50° C., and then it proceeds at a temperature of about 80° C. However, other reaction conditions may be employed, the choice thereof being still within the knowledge of one skilled in the art.

For its purification and isolation, the compound of formula (I), advantageously the compound of formula (Ia), is preferably washed several times with acidic water and with water, at a high temperature in the range from 60 to 80° C., so as to melt it during the washings, and then the temperature of the mixture is decreased up to 0-10° C. in order to promote the solidification of the product which is recovered by filtration.

It has been observed that the addition of small amounts of specific additives to the water used for the last washing before cooling and solidification occur, promotes the formation of the desired compound with a particle size suitable for its use while allowing the compound to be more easily discharged from the reactor.

In fact, it has been found that the addition of small proportions of additives such as non-ionic surfactants, for example secondary alcohol ethoxylates such as "Tergisol 15-S-9®" or acetone, increases the wettability of the product and highly promotes the solidification thereof as a fine powder during the cooling step, thereby making the product easier to be discharged from industrial reactors and avoiding the formation of lumps and scales on the walls and stirrers within the reactor.

Particularly, these surfactants, for example Tergisol 15-S-9®, have been shown to be useful at concentrations of 0.05-1% (weight/weight) with respect to the water used in the reaction, for example at concentrations of about 0.1%.

Acetone, which is a preferred additive according to the present invention, has been shown to be very effective at concentrations of 0.1-20%, for example about 5% (weight/weight), with respect to the water used in the reaction.

Thus, according to a preferred embodiment, the process of the invention comprises adding an additive selected from secondary alcohol ethoxylates, such as "Tergisol 15-S-9®" and acetone, while the compound of formula (I), advantageously the compound of formula (Ia), is subjected to the final washing with water, in order to obtain a better particle size and allow the compound of formula (I) to be isolated more easily.

The compounds of formula (II) and (III) are reacted in substantially stoichiometric amounts to give the desired compound of formula (I).

The amine-type base used should salify the acids produced during the reaction (HF and HX). Therefore, it is preferred that the base is used in a molar amount which is at least twice the molar amount of the compounds of formula (II) or (III).

The reaction is completed within a few hours, depending on the charged amount of reactants; one skilled in the art can follow the progress of the reaction by conventional methods.

At the end of the reaction, the reactor is either allowed to cool or actively cooled, and the compound of formula (I) is isolated. By way of an example, the compound can be isolated by separating it from the reaction mother liquors.

The compound of formula (I) is obtained in a highly pure form. However, if desired or necessary, the compound can be further purified, for example by washing it with water and then isolating it.

Therefore, according to the process of the invention, the compound of formula (I), and particularly the preferred compound of formula (Ia), can be obtained in a pure form free from metal contamination, and thus in a form which is suitable for the use thereof as an additive for polymers.

Detailed examples of how the reaction of the process of the invention can be carried out are provided in the Experimental Section of the present specification.

EXPERIMENTAL SECTION

Example 1

Preparation of tetrabutylphosphonium nonafluorobutane-1-sulfonate with Trimethylamine Equipment: 1-liter reactor with discharge at the bottom, mechanical stirring means, cooling means, thermometer, metering funnel. The reactor is loaded with 204.0 g of demineralized water, 47.0 g of a 45% aqueous solution of trimethylamine, and 79.8 g of a 75% aqueous solution of tetrabutylphosphonium bromide. The mixture is brought to 50° C., and then 50.0 g of nonafluorobutane-1-sulfonyl fluoride is metered over about 45 minutes. When the addition is completed, the mass is heated to 80° C. and maintained at that temperature for 3 hours in order to complete the reaction. Cool to 60° C. and wait for the separation of the phases, then discharge 91.9 g of crude, melted tetrabutylphosphonium nonafluorobutane-1-sulfonate and 281.6 g of reaction mother liquors. The product is washed with demineralized water at 60° C. (2×200 g, 1 hour each) thereby obtaining 86.4 g of derivative. Thereafter, the tetrabutylphosphonium nonafluorobutane-1-sulfonate is re-charged into the reactor along with 200.9 g of demineralized water, the mixture is brought to 60° C. and cooled to promote the precipitation of the product (between 30-40° C.). After filtration and drying, 77.8 g of purified tetrabutylphosphonium nonafluorobutane-1-sulfonate is isolated (86% molar yield).

Characterization: identification via LC-MS (purity: % titration area 99.5%).

Example 2

Preparation of tetrabutylphosphonium nonafluorobutane-1-sulfonate with Ammonia Equipment: 1-liter reactor with discharge at the bottom, mechanical stirring means, cooling means, thermometer, metering funnel. The reactor is loaded with 400.1 g of demineralized water followed by 95.0 g of a 28% aqueous solution of $NH_3$ and 150.0 g of 75% tetrabutylphosphonium bromide in water. The mass is heated to 50° C., and 100.4 g of nonafluorobutane-1-sulfonyl fluoride is metered over about 1 hour. When the metering is completed, the reaction is brought to completion at 80° C. for 3 hours.

It is cooled to 60° C. to separate the product, which is obtained as a heavy, melted phase, 186.0 g of crude tetrabutylphosphonium nonafluorobutane-1-sulfonate and 553.6 g of synthesis mother liquors. The product is washed with demineralized water (2×400 g at 60° C., 1 hour each), thereby obtaining 179.5 g of washed tetrabutylphosphonium nonafluorobutane-1-sulfonate. The product is charged into the reactor along with 400.3 g of demineralized water, and the mass is brought to 60° C. and then cooled to allow the product to precipitate. After filtration and drying at 50° C. under reduced pressure, 135.5 g of dried tetrabutylphosphonium nonafluorobutane-1-sulfonate is obtained. (molar yield <89%).

Characterization: identification via LC-MS (% titration area: 90.8%).

Example 3

Preparation of tetrabutylphosphonium nonafluorobutane-1-sulfonate with Ammonia Equipment: 1-liter reactor with discharge at the bottom, mechanical stirring means, cooling means, thermometer, metering funnel. The reactor is loaded with 200.5 g of demineralized water, 28 g of a 28% solution of $NH_3$ and 80.4 g of a 75% solution of tetrabutylphosphonium bromide. The mass is brought to a temperature of 50° C., then 50.0 g of nonafluorobutane-1-sulfonyl fluoride is started to be metered over a time period of approximately 1.5 hours. When the metering is completed, the reaction is heated to 80° C. and maintained for 3 hours in order to complete it. It is cooled to 60° C. and two phases are separated: 89.7 g of a melted product as a heavy phase and 260.8 g of reaction mother liquors. Then, the product is washed (2×200 g of demineralized water at 60° C.×1 hour each), in each case followed by a separation of the phases at 60° C. In this way, 80.7 g of washed tetrabutylphosphonium nonafluorobutane-1-sulfonate is obtained. The reactor is charged with 200.7 g of demineralized water and the above-isolated product, the whole is heated to 60° C. followed by cooling to allow for the precipitation of tetrabutylphosphonium nonafluorobutane-1-sulfonate, which occurs at a temperature between 30 and 40° C.

The product is filtered and dried at 45° C. under reduced pressure, thereby eventually obtaining 72.5 g of pure tetrabutylphosphonium nonafluorobutane-1-sulfonate derivative (molar yield <80%).

Characterization: identification via LC-MS (purity: % titration area 94.4%).

Example 4

Preparation of tetrabutylphosphonium nonafluorobutane-1-sulfonate with Tetramethylammonium Hydroxide Equipment: 1-liter reactor with discharge at the bottom, mechanical stirring means, cooling means, thermometer, metering funnel. The reactor is loaded with 300.6 g of demineralized water, 246.0 g of a 25% aqueous solution of tetramethylammonium hydroxide, and 150.0 g of a 75% aqueous solution of tetrabutylphosphonium bromide. The mixture is brought to 50° C., and then 100.5 g of nonafluorobutane-1-sulfonyl fluoride is metered over about 1 hour. When the addition is completed, the mass is heated to 80° C. and maintained at that temperature for 3.5 hours in order to complete the reaction. Cool to 60° C. and wait for the separation of the phases, then discharge 185.5 g of crude, melted tetrabutylphosphonium nonafluorobutane-1-sulfonate and 606.7 g of reaction mother liquors. The product is washed with demineralized water at 60° C. (2×400 g, 1 hour each) thereby obtaining 181.3 g of wet derivative. Thereafter, the tetrabutylphosphonium nonafluorobutane-1-sulfonate is re-charged into the reactor along with 400.3 g of demineralized water, the mixture is brought to 60° C., and the product is separated as a melted solid, thereby eventually obtaining 171.5 g of tetrabutylphosphonium nonafluorobutane-1-sulfonate.

Characterization: identification via LC-MS (purity: % titration area 99.5%).

Example 5

Preparation of tetrabutylphosphonium nonafluorobutane-1-sulfonate with Triethylamine Equipment: 1-liter reactor with discharge at the bottom, mechanical stirring means, cooling means, thermometer, metering funnel. The reactor is loaded with 231.0 g of demineralized water, 36.1 g of triethylamine, and 79.8 g of a 75% aqueous solution of tetrabutylphosphonium bromide. The mixture is brought to 50° C., and then 50.0 g of nonafluorobutane-1-sulfonyl fluoride is metered over 1 hour. When the addition is completed, the mass is heated to 80° C. and maintained at that temperature for 3 hours in order to complete the reaction. Cool to 60° C. and wait for the separation of the phases, then discharge 94.4 g of crude, melted tetrabutylphosphonium nonafluorobutane-1-sulfonate and 299.5 g of reaction mother liquors. The product is washed with 200 g of 1.5% $H_2SO_4$ in water and then with 202 g of demineralized water at 60° C. (1 hour each), thereby obtaining 88.7 g of washed, wet tetrabutylphosphonium nonafluorobutane-1-sulfonate. Thereafter, the tetrabutylphosphonium nonafluorobutane-1-sulfonate is re-charged into the reactor along with 206.8 g of demineralized water, the mixture is brought to 60° C., and the product is separated as a melted solid, thereby obtaining 87.4 g of tetrabutylphosphonium nonafluorobutane-1-sulfonate. After drying on a rotovap under reduced pressure, 84.3 g of dried tetrabutylphosphonium nonafluorobutane-1-sulfonate is eventually isolated. Characterization: identification via LC-MS (purity: % titration area 99.5%)

Example 6

Purification and Isolation of tetrabutyl phosphonium nonafluorobutane-1-sulfonate with Addition of Tergisol 15-S-9

Equipment: 1000-ml jacketed reactor equipped with mechanical stirring paddle, thermometer, bubble cooling means and discharge at the bottom.

Procedure: load water containing 0.1% Tergisol (369 g), heat to 60° C., and load crude, melted tetrabutyl phosphonium nonafluorobutane-1-sulfonate (123 g). Set a cooling ramp up to 20° C. over 12 hours. At 20° C., the product appears as a well-suspended white solid. The product is filtered, and the filtered solid is washed with 185 g of demineralized water. Dry on a rotovap up to 45° C. (residual 25 mbars), thereby obtaining 113 g of dried product as a white powder.

Example 7

Isolation of tetrabutyl phosphonium nonafluorobutane-1-sulfonate with Addition of Acetone Equipment: 1000-ml jacketed reactor equipped with mechanical stirring paddle, thermometer, bubble cooling means and discharge at the bottom.

Procedure: load water (487 g) and acetone (26 g), heat to 60° C., and load crude, melted tetrabutyl phosphonium nonafluorobutane-1-sulfonate (171 g). Set a cooling ramp up to 20° C. over 12 hours. At 20° C., the product appears as a well-suspended white solid. Cool to 1° C. over 6 hours and filter. The filtered solid is washed with 170 g of demineralized water. Dry on a rotovap up to 45° C. (residual 25 mbars), thereby obtaining 163 g of dried product as a white powder.

The invention claimed is:

1. Process for preparing compounds of formula (I)

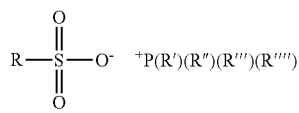
(I)

wherein

R is a straight or branched, saturated or unsaturated, fluoroalkyl group having 1 to 10 carbon atoms, with said fluoroalkyl being optionally interrupted by —O—, —S— or —$NR_1$—, wherein $R_1$ is a hydrogen or a perfluoroalkyl group having 1 to 8 carbon atoms, and R', R'', R''' and R'''' are the same or different, and represent a hydrogen atom or a straight or branched, saturated or unsaturated, alkyl group having 1 to 10 carbon atoms, with said alkyl being optionally interrupted by —O—, —S— or —$NR_2$— wherein $R_2$ is a hydrogen or an alkyl group having 1 to 10 carbon atoms, comprising reacting a compound of formula (II)

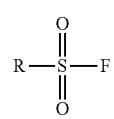
(II)

wherein R is defined as above, with a compound of formula (III)

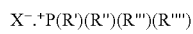
(III)

wherein R', R'', R''' and R'''' are defined as above, and $X^-$ represents a halide or a hydroxide ion, in the presence of an amine-type base.

2. Process according to claim 1, wherein R is a straight perfluoro alkyl group having 2 to 8 carbon atoms.

3. Process according to claim 2, wherein R is a nonafluorobutyl group.

4. Process according to claim 1, wherein R', R'', R''' and R'''' are a butyl group.

5. Process according to claim 1, wherein the amine-type base is selected from alkyl-, dialkyl- and trialkyl-amine, ethanolamine, morpholine, piperazine, piperidine, quinuclidine, pyridine and aniline.

6. Process according to claim 1, wherein the amine-type base is selected from trimethylamine, triethylamine, tributylamine, ammonium hydroxide and tetra-alkyl ammonium hydroxide.

7. Process according to claim 1, wherein $X^-$ is $Br^-$.

8. Process according to claim 1, for preparing the tetrabutylphosphonium nonafluorobutane-1-sulfonate of formula (Ia)

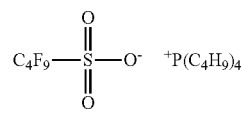
(Ia)

comprising reacting perfluoro butyl sulfonyl fluoride with tetrabutylphosphonium bromide in aqueous medium, in the presence of an amine-type base selected from trimethylamine, triethylamine, tributylamine, ammonium hydroxide and tetra-alkyl ammonium hydroxide.

9. Process according to claim 1, wherein the amine-type base is used in a molar amount at least twice the molar amount of the compounds of formula (II) or (III).

10. Process according to claim 1, wherein the reaction is carried out at a temperature comprised between room temperature and the reflux temperature of the reaction mixture.

11. Process according to claim 1, which comprises isolating the compound of formula (I) after washing it with water in the presence of an additive selected from non-ionic surfactants and acetone.

12. Process according to claim 11, characterized in that said additive is acetone.

13. Process according to claim 12, characterized in that said acetone is present at concentrations of 0.1-20% (w/w) with respect to the water used for washing.

14. Process according to claim 13, characterized in that said acetone is present at a concentration of 5% (w/w) with respect to the water used for washing.

\* \* \* \* \*